United States Patent [19]
Narayanan et al.

[11] Patent Number: 5,588,436
[45] Date of Patent: Dec. 31, 1996

[54] PULSED DOPPLER PROBE

[75] Inventors: Krishna Narayanan, Pittsburgh; Vasant Padmanabhan, Monroeville; Fredrick J. Shipko, Spring Church; Louis Goode, Evans City, all of Pa.; Neal E. Fearnot, West Lafayette, Ind.

[73] Assignees: Cook Pacemaker Corporation, Leechburg, Pa.; MED Institute, West Lafayette, Ind.

[21] Appl. No.: 540,852

[22] Filed: Oct. 11, 1995

[51] Int. Cl.⁶ ........................................... A61B 8/00
[52] U.S. Cl. ............... 128/662.03; 128/661.08; 128/691
[58] Field of Search ............... 128/660.09, 660.10, 128/661.07, 661.08, 661.09, 662.03, 662.01, 691

[56] References Cited

U.S. PATENT DOCUMENTS

| | | | |
|---|---|---|---|
| 3,661,146 | 5/1972 | Peronneau et al. | |
| 4,355,643 | 10/1982 | Laughlin et al. | |
| 4,541,433 | 9/1985 | Baudino | |
| 4,915,113 | 4/1990 | Holman | |
| 4,926,875 | 5/1990 | Rabinovitz et al. | |
| 4,947,854 | 8/1990 | Rabinovitz et al. | |
| 5,152,293 | 10/1992 | Venesh et al. | 128/662.03 |
| 5,205,292 | 4/1993 | Czar et al. | 128/662.03 |
| 5,289,821 | 3/1994 | Swartz | |

OTHER PUBLICATIONS

Swartz, W. M., M.D. et al.; "Direct Monitoring of Microvascular Anastomoses with the 20–MHz Ultrasonic Doppler Probe:" An Experimental and Clinical Study; Plastic and Reconstructive Surgery; Feb. 1988, vol. 81, No. 2, pp. 159–161.

Swartz, W. M., M.D. et al.; "Implantable Venous Doppler Microvascular Monitoring: Laboratory Investigation and Clinical Results"; Plastic And Reconstructive Surgery; Jan. 1994; vol. 93, No. 1, pp. 152–163.

*Primary Examiner*—George Manuel
*Attorney, Agent, or Firm*—Richard J. Godlewski

[57] ABSTRACT

A pulsed Doppler probe 10 for monitoring blood flow within a blood vessel 12 includes a sheath 17 and a plurality of electrically conductive wires 26 extending through the sheath 17. The wires 26 have distal ends 28 to which an ultrasonic transducer 18 is operatively connected. The transducer 18 has an operative surface 20, and the probe 10 also includes a means 22 for fixing the orientation of the operative surface 20 with respect to at least one of a longitudinal axis 38 of the sheath 17, and the orientation fixing means 22, or with respect to the distal ends 28 of the electrically conductive wires 26. The orientation fixing means 22 includes an epoxy material 24 encasing the ultrasonic transducer 18, shaped to include a cylindrically concave surface 30. The probe 10 further includes a mesh band 44 of at least one of an absorbable material and an inert material adapted to encircle the blood vessel 12. The probe 10 also includes a remotely operable means 46 for detachably securing the orientation fixing means 22 to the mesh band 44 so that the ultrasonic transducer 18 is positioned adjacent to the blood vessel 12 with the concave surface 30 of the encasing material 24 facing the blood vessel 12.

20 Claims, 3 Drawing Sheets

PULSED DOPPLER PROBE

Technical Field

This invention relates generally to medical devices, and more particularly to devices for monitoring the flow of blood in a blood vessel during or after a surgical procedure.

BACKGROUND OF THE INVENTION

A variety of microsurgical procedures have been developed which have saved the lives of patients and/or improved the quality of life for patients. Such procedures include organ transfer surgery, reconstructive surgery following the removal of tumors (particularly in the areas of the head and neck), CABG procedures, and reconstructive surgery such as free tissue transfer and the like. Free tissue transfer entails the removal of tissue and/or muscle from one part of the body, along with an associated artery and vein, and the reattachment of the tissue and/or muscle to another part of the body. The artery and vein of the transferred tissue and/or muscle are then anastomosed (that is, connected) to a native artery and vein in order to achieve blood circulation in the transferred tissue and/or muscle.

The success of such transfer lies in obtaining good patency of the anastomosis, and hence good patency in the transferred tissue and/or muscle (sometimes referred to as the flap). The primary complication in microvascular surgery such as free tissue transfer is thrombosis. Unrecognized thrombosis reduces patency in the flap and reduces the probability of salvaging the flap. The window of opportunity for salvage after thrombosis is presently believed to be only about six hours of warm ischemia. It is therefore critical that any vascular thrombosis in a transferred flap be recognized and any resulting ischemia be remedied as soon as possible. While the success rate of the free tissue transfer procedure is quite good, believed to be about 90% on average, failure rates have been reported ranging from 6% to 21%. Even though these are fairly low, any surgical failure can be costly in several ways, and it would of course be highly desirable to reduce the failure rate of this and similar techniques.

A variety of operative and post-operative monitoring techniques are presently used for clinically assessing thrombosis and identifying the resulting ischemia. Electromagnetic flowmetry is a definitive technique to monitor blood flow; but so far this technique has proven too difficult to use in free tissue transfer. Some of the other techniques that have been clinically studied include intravenous fluorescein, transcutaneous oxygen, tissue pH, pulse oximetry, muscle contractility, temperature, photoplethysmography, electrical impedance plethysography, and the like. Unfortunately; these techniques are not useful for monitoring bone flaps or other flaps which are located well below the skin, that is, buried. Newer techniques include surface temperature measurement, $pO_2$ monitoring, and laser Doppler flowmeters, but these also require the presence of an exposed portion of the flap, and are of no benefit for monitoring bone or buried flaps. Moreover, none of these techniques evaluates the flow of blood at the microvascular anastomoses directly. Thus, no technique has been universally accepted as an adequate monitor of thrombosis.

One assessment technique gaining wider acceptance is the use of an implantable ultrasonic Doppler probe positioned directly on the anastomosed vein and/or the artery. Such a probe includes an implanted piezoelectric transducer carried on a band or sleeve attached directly on the blood vessel of interest. The transducer is used to alternately generate ultrasonic waves and measure backscattering of those waves. Since blood is a very effective backscattering medium, the Doppler shift in the frequency of the backscattered ultrasonic waves yields a precise and accurate measurement of the blood velocity (and, by implication from the cross-sectioned area of the blood vessel, the volume of blood flow) in the vessel of interest. Signals relating to the phasic velocity and mean velocity of the blood can also be obtained. The Doppler probe is thus advantageous over prior techniques in that it permits easy monitoring of vascular patency in even buried flaps, and can be used to monitor patency continuously over a period of days. Careful monitoring of blood flow should provide a sufficiently early warning of thrombosis that the chances of salvaging the flap are significantly increased.

Unfortunately, the use of known ultrasonic Doppler probes and techniques has been subject to a number of drawbacks. The two most significant drawbacks have been the inability to securely place the probe on the blood vessel (perivascularly), and thus ensure proper orientation of the operative surface of the piezoelectric transducer, so as to acquire reliable signals from the transducer; and the difficulty of removing the probe from the vicinity of the blood vessel without the use of anaesthesia, or without performing an additional surgical incision or reopening an old incision.

For example, U.S. Pat. No. 5,289,821 (William M. Swartz, Mar. 1, 1994) discloses a device in which electrically conductive wires carrying an ultrasonic transducer are connected by a silicone adhesive to a biologically inert or absorbable strip, the strip being wrapped about the blood vessel of interest. After three to seven days, when monitoring is complete, an incision is made to detach the wires from the strip, and the transducer removed from the patient by pulling on the wires. While the patent asserts that this new incision is very small, it is difficult to see how a practitioner could withdraw the transducer, wire, and the sealant without causing trauma to the surrounding tissue or, even worse, the anastomosed vessel. To minimize this removal trauma, the practitioner would normally make the incision large enough to permit this withdrawal. However, the enlarged incision would cause unnecessary discomfort to the patient. Moreover, the device lacks structure to maintain orientation of the transducer during introduction to and implantation on the blood vessel, or from breaking off the transducer and/or the wires during removal. Failure to maintain proper orientation of the transducer can lead to false blood flow or velocity readings and as a result cause further surgical intervention with associated patient discomfort and prolongation of the monitoring process.

Other known devices and techniques have their own drawbacks. Accordingly, it would be highly desirable to achieve a device for monitoring blood flow during or after a surgical procedure which can be easily and quickly attached to a blood vessel. It would also be highly desirable that such a probe be firmly attachable to the blood vessel, such that reliable and repetitive monitoring signals be acquired for the period necessary to ensure patency of the surgical procedure, for example, for at least three weeks. It would also be advantageous for such a probe to be easily removable from the patient without entailing the performance of additional invasive procedures; ideally, the probe would be removable at the patient's bedside, with an ease equal to that of removing a conventional drainage catheter. It is also desirable that such a probe be useful with arteries as well as veins, and be useful for monitoring vessels having a range of diameters, particularly, those above 1 mm diameter. Of course, it would be essential to ensure that the orientation of the operative surface of the ultrasonic transducer be fixed, and to reduce or eliminate any potential for detachment of the transducer from the probe or sheath carrying it.

SUMMARY OF THE INVENTION

The foregoing problems are solved and a technical advance is achieved in an illustrative pulsed Doppler probe for monitoring and, preferably, measuring blood velocity within a blood vessel. The probe of the present invention first comprises a longitudinally extending sheath and a plurality of electrically conductive wires extending longitudinally through the sheath. The probe also comprises an ultrasonic transducer that has an operative surface and is operatively connected to the distal ends of the conductive wires. The orientation of the operative surface is fixed by an orientation fixing means carried by the sheath and is also fixed with respect to at least one of the longitudinally extending wires or the longitudinal axis of the orientation fixing means or the sheath. In operation, the longitudinally extending wires or the axis of the sheath or the orientation fixing means is positioned parallel to the axis of the blood vessel so that the operative surface of the transducer is positioned relative to the axis of the blood vessel.

The orientation fixing means preferably includes an epoxy material encasing the ultrasonic transducer and the distal ends of the wires, the material being shaped to include a cylindrically concave surface. As a result, the orientation of the transducer is also fixed with respect to the concave surface. The probe preferably includes a plural bore ceramic tube connecting the sheath and the orientation fixing means, through which the wires pass. The probe further includes a mesh band that is at least one of an absorbable material and an inert material adapted to encircle the blood vessel.

The probe also comprises a remotely operable means for detachably securing the orientation fixing means to the mesh band so that the ultrasonic transducer is positioned adjacent to the blood vessel with the concave surface of the encasing material facing the blood vessel. The detachable securing means preferably includes: (a) a transverse bore through the encasing material; (b) a longitudinally extending severable thread slidably passing through the transverse bore and the sheath, the thread including first and second free ends external to the sheath and remote from the encasing material; and (c) a longitudinally split, removable collar on the sheath, positioned over the free ends of the thread, frictionally retaining the free ends of the thread against the sheath.

The sheath and the orientation fixing means are preferably isodiametric, that is, they are generally circular in cross-section and have substantially the same diameter, thereby facilitating removal of the probe upon operation of the securing means. Advantageously, the diameter of the sheath and the orientation fixing means are about the same as the blood vessel which the probe is intended to monitor. For example, if the blood vessel of interest has a diameter of about 4 mm downstream of the anastomosis, the sheath and orientation fixing means can have a diameter in range of about 0.5 to 2 mm and, preferably, 2 mm.

In a first aspect, then, the present invention is directed to a pulsed Doppler probe for monitoring and preferably measuring blood velocity within a blood vessel, comprising: a plurality of longitudinally extending electrically conductive wires having distal ends; an ultrasonic transducer operatively connected to the distal ends of the wires, the transducer having an operative surface; means having a longitudinal axis and fixing the orientation of the operative surface of the ultrasonic transducer with respect to at least one of the longitudinally extending electrically conductive wires or the longitudinal axis of the orientation fixing means; a band adapted to encircle the blood vessel; and remotely operable means for detachably securing the orientation fixing means to the band so that the ultrasonic transducer is positioned adjacent to the blood vessel; whereby remote operation of the securing means permits withdrawal of the ultrasonic transducer, wires and orientation fixing means from the blood vessel while leaving the band encircled about the blood vessel. This first aspect of the invention is also directed to various additional elements identified above.

In a second aspect, the present invention is directed to a pulsed Doppler probe for monitoring and preferably measuring blood velocity within a blood vessel, comprising: a longitudinally extending sheath having a longitudinal axis; a plurality of electrically conductive wires extending longitudinally through the sheath, the wires having distal ends; an ultrasonic transducer operatively connected to the distal ends of the wires, the transducer having an operative surface; means having a longitudinal axis and fixing the orientation of the operative surface of the ultrasonic transducer with respect to at least one of the longitudinally extending electrically conductive wires and the longitudinal axis (38), and of the orientation fixing means (22) and the sheath (17) the orientation fixing means comprising an epoxy material encasing the ultrasonic transducer and shaped to include a cylindrically concave surface; a mesh band of at least one of an absorbable material and an inert material, adapted to encircle the blood vessel; and remotely operable means for detachably securing the orientation fixing means to the mesh band so that the ultrasonic transducer is positioned adjacent to the blood vessel and the concave surface of the encasing material facing the blood vessel; wherein the securing means comprises: (a) a transverse bore through the encasing material; and (b) a longitudinally extending severable thread slidably passing through the transverse bore and the sheath, the thread including first and second free ends external to the sheath and remote from the encasing material; and wherein the sheath and the orientation fixing means are generally circular in cross-section and have substantially the same diameter, thereby facilitating removal of the probe upon operation of the securing means. This second aspect is also directed to such a probe in which the securing means further comprises a removable collar on the sheath, positioned over the first and second free ends of the thread so as to frictionally retain the first and second free ends of the thread against the sheath.

In a final aspect, the present invention is directed to a pulsed Doppler probe for monitoring and preferably measuring blood velocity within a blood vessel, comprising: a longitudinally extending sheath having a longitudinal axis; a plurality of electrically conductive wires extending longitudinally through the sheath, the wires having distal ends; an ultrasonic transducer operatively connected to the distal ends of the wires, the transducer having an operative surface; means having a longitudinal axis and fixing the orientation of the operative surface of the ultrasonic transducer with respect to at least one of the longitudinally extending wires and the axis of the means and the sheath, the orientation fixing means comprising an epoxy material encasing the ultrasonic transducer and shaped to include a cylindrically concave surface; a ceramic tube connecting the sheath and the orientation fixing means, the wires passing through the ceramic tube; a mesh band of at least one of an absorbable material and an inert material adapted to encircle the blood vessel; and remotely operable means for detachably securing the orientation fixing means to the mesh band so that the ultrasonic transducer is positioned adjacent to the blood vessel and the concave surface of the encasing material faces the blood vessel; wherein the securing means comprises: (a) a transverse bore through the encasing material; (b) a longitudinally extending severable thread slidably passing through the transverse bore and the sheath, the thread including first and second free ends external to the sheath and remote from the encasing material; and (c) a removable collar on the sheath, positioned over the first and second free ends of the thread so as to frictionally retain the first and second free ends of the thread against the sheath; and wherein the sheath and the orientation fixing means are generally circular in cross-section and have substantially the same diameter, thereby facilitating removal of the probe upon operation of the securing means.

BRIEF DESCRIPTION OF THE DRAWINGS

A better understanding of the present invention will now be had upon reference to the following detailed description, when read in conjunction with the accompanying drawing, wherein like reference characters refer to like parts throughout the several views, and in which.

DETAILED DESCRIPTION

Figure 1:
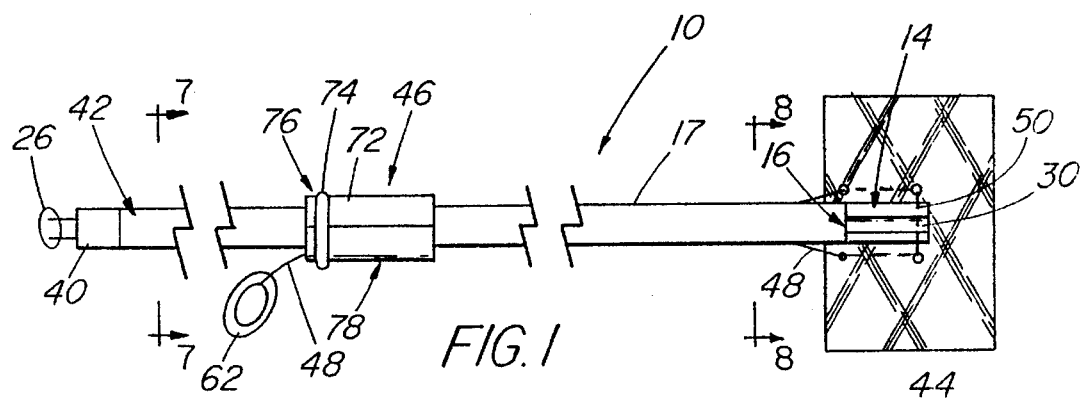
FIG. 1 is a bottom view of the preferred embodiment of the present invention.
Figure 9:
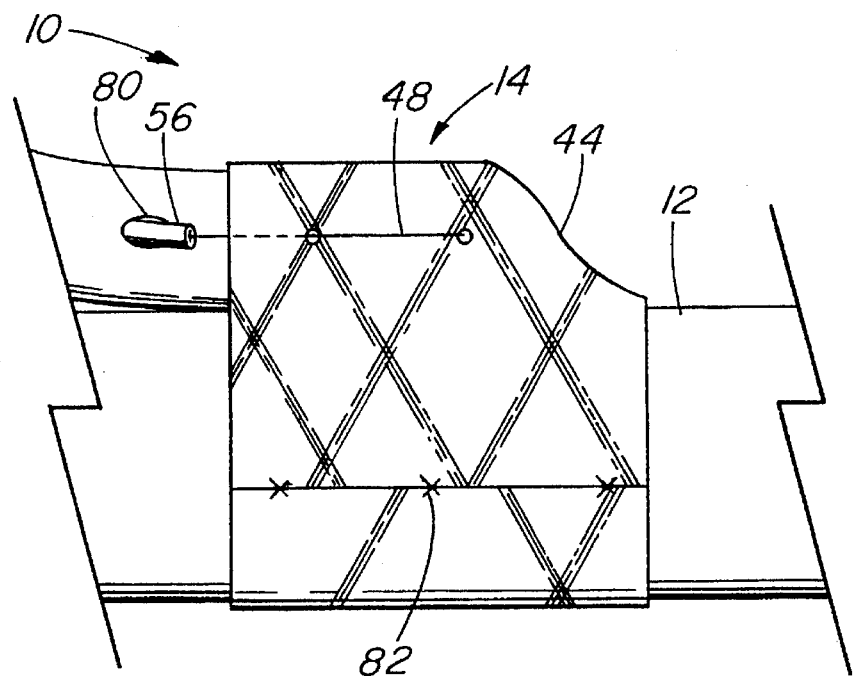
FIG. 9 is an enlarged view of a portion of the preferred embodiment of the present invention during use.

FIGS. 1 and 9 depict the preferred embodiment of the present invention as a pulsed Doppler probe 10 positionable against a blood vessel 12. It is an advantage of the present invention that the probe 10 can be positioned on a blood vessel 12 which is either arterial or venous.

Figure 2:
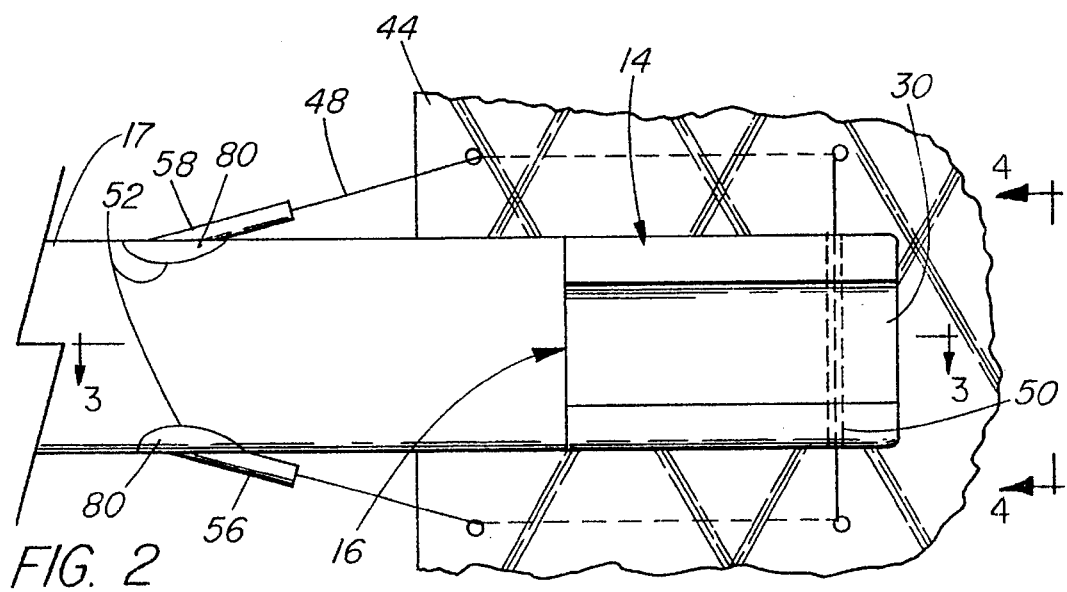
FIG. 2 is an enlarged bottom view of a distal portion of the preferred embodiment of the present invention of FIG. 1.
Figure 3:
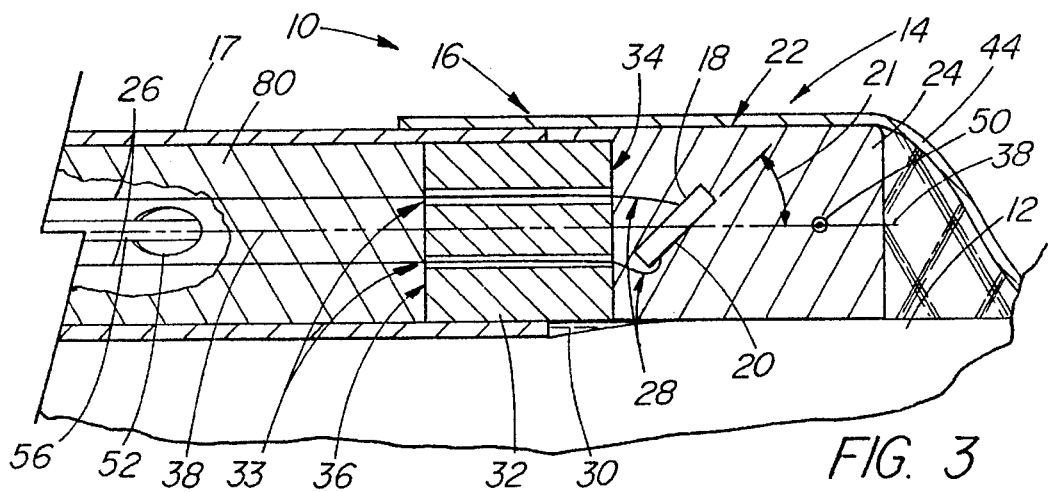
FIG. 3 is a cross-sectioned side view taken along line 3—3 in FIG. 2 of the preferred embodiment of the present invention adjacent a blood vessel.
Figure 7:
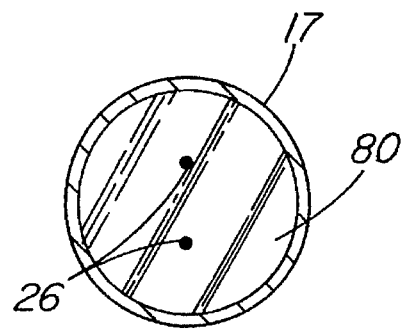
FIG. 7 is a cross-sectional view of the present invention taken along line 7—7 in FIG. 1.
Figure 8:
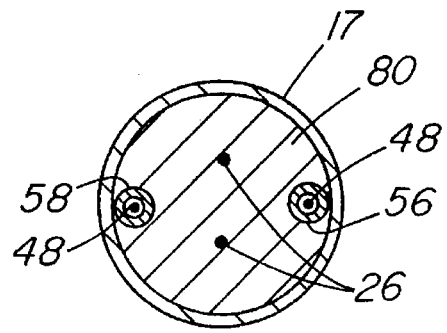
FIG. 8 is a cross-sectional view of the present invention taken along line 8—8 in FIG. 1.

With additional attention to FIGS. 2 and 3, the probe 10 first comprises a sheath 17 carrying at its distal end 16 a transducer head 14. The sheath 17 can be composed of any medical grade, biocompatible material, for example, PVC. For use with blood vessels of about 1–16 mm diameter, the sheath diameter can conveniently be about 6 French (2 mm). A plurality of and preferably two insulated, electrically conductive wires 26 are positioned in and extend longitudinally through the sheath 17. The transducer head 14 comprises an ultrasonic piezoelectric transducer 18 that is operatively connected to the distal ends 28 of the wires 26. The wires 26 are preferably 0.005 inch diameter insulated copper wires, although other materials are of course also suitable. Connection of the transducer 18 to the wires 26 can be made in any conventional manner, for example, by soldering or adhesive. The transducer 18 has an operative surface 20 facing the blood vessel 12 at angle 21 of about 30 to 60 degrees, preferably at an angle of about 45 degrees with respect to the longitudinally extending wires 26 or longitudinal axis 38 of the sheath 17 or head 14. Conveniently, as shown in FIGS. 7 and 8, the insulated wires 26 are contained within sheath 17, and the unoccupied space within the sheath 17 about its distal end is filled with silicone 80.

With reference again to FIGS. 1–3, the transducer head 14 of the probe 10 also comprises a means 22 for fixing the orientation of the operative surface 20 with respect to at least one of the longitudinally extending wires 26, sheath 17, or head 14. However, in use, the orientation of operative surface 20 should be positioned and fixed with respect to the longitudinal axis of the blood vessel. Most conveniently, the orientation fixing means 22 comprises a material 24 encasing the ultrasonic transducer 18 and the distal ends 28 of the wires 26. The encasing material can be any medical grade, biocompatible material, which transmits ultrasound waves sufficiently well to achieve good signal strength during use of the probe 10. Conveniently, the encasing material 24 is an epoxy, but a variety of other materials are useful as well.

The sheath 17 thus carries at its distal end 16 both the ultrasonic transducer 18 and the orientation fixing means 22. A conventional plug 40 is carried on the proximal, remote end 42 of the sheath 17, opposite distal end 16, for connection of the electrically conductive wires 26 to an appropriate ultrasound frequency generator, back-scattering sensor and suitable computer control equipment (not shown). The nature of these devices is not believed to be critical to the present invention, and their selection and use should be well within the ability of those of even rudimentary skilled in the art. By way of example, however, it has been found convenient to use a 20 MHz piezoelectric transducer 18 energized by a 20 MHz pulsed ultrasound energy generated by a PD-20 Doppler Velocimeter (Crystal Biotech Inc.), with a pulse repetition (burst) frequency of 62.5 KHz and 8 cycles per burst. The range gate for such equipment can vary from 1 mm to 10 mm, employed with a sample volume of about 1 $mm^3$. This yields about 1 mm as the smallest vessel diameter with which this equipment is useful.

With additional reference to FIG. 3, it has been found convenient during construction of the probe 10 of the present invention to include a ceramic tube 32 at the distal end 16 of the sheath 17 for connecting the transducer head 14 to the sheath 17, and in particular, for connecting the orientation fixing means 22 to the sheath 17. The ceramic tube 32 includes at least one and preferably two longitudinal throughbores 33 in which the wires 26 are disposed. Preferably, a proximal remote end 36 of the ceramic tube 32 is received in the bore of the sheath 17 at the distal end 16, and a distal end 34 of the tube 32 is encased in the orientation fixing means 22.

Figure 4:
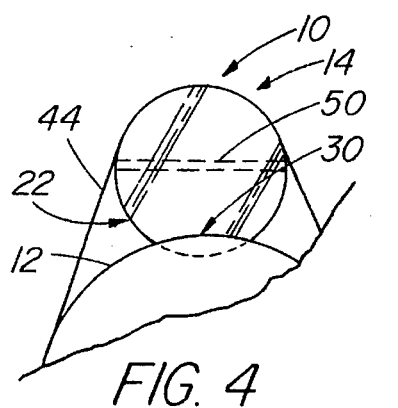
FIG. 4 is an end view taken from line 4—4 in FIG. 2.
Figure 6:
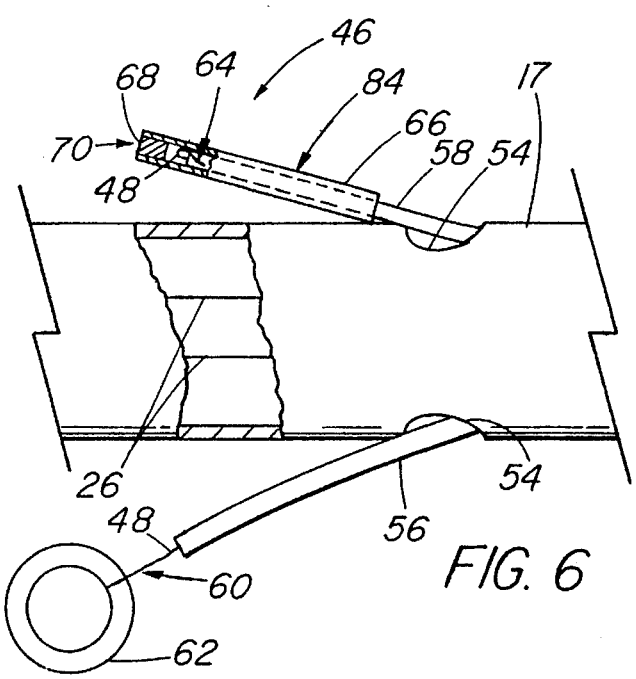
FIG. 6 is a partially sectioned and enlarged view of the mid portion of the preferred embodiment of the present invention of FIG. 5 with a collar positioned therearound.

With respect to the particular configuration of the sheath 17 and the orientation fixing means 22, it is highly preferred that the sheath 17 and the orientation fixing means 22 are generally circular in cross-section and be isodiametric, that is, that they have substantially the same diameter, so as to facilitate smooth removal of the probe 10 from the vicinity of the blood vessel 12 without surgical intervention, incision, anaesthesia or significant discomfort to the patient. As a result, the longitudinal axis of the sheath and head should coincide. By way of example, if the blood vessel 12 is about 4 mm in diameter, the diameter of the sheath 17 and the orientation fixing means 22 should be in range of about 0.5 to 2 mm and, preferably, 2 mm for a 4 mm or larger vessel. However, as shown in FIG. 4, it is also convenient that the orientation fixing means 22 be shaped to include a slightly cylindrically concave surface 30 facing the blood vessel 12. This serves to both orient the transducer head 14 and improve the transmission of ultrasound waves between the transducer 18 and the interior of the blood vessel 12. This also prevents the transducer head from rotating on the blood vessel.

With continued reference to FIGS. 1, 2, and 9, the probe 10 of the present invention also comprises a band 44 carried on the sheath 17 adjacent to the transducer head 14. The band 44 is adapted to encircle the blood vessel 12 and hold the transducer head 14 against the blood vessel 12. The band 44 can be composed of any medical grade, biocompatible absorbable and/or inert material and is preferably configured as a mesh. The band 44 is most preferably composed of Vicryl™ mesh (Ethicon, Inc.) and is secured closely about the blood vessel 12 in any convenient fashion, for example, by a plurality of medical grade, biocompatible sutures 82.

The probe 10 of the present invention further comprises a remotely operable means 46 for detachably securing the transducer head 14 and, in particular, orientation fixing means 22 to the band 44, so that the ultrasonic transducer 18 is positioned adjacent to the blood vessel 12, and that the operative surface 20 of the transducer 18 is held in position facing the blood vessel 12. Remote operation of the securing means 46 permits withdrawal of the transducer head 14 (the ultrasonic transducer 18 and the orientation fixing means 22) and the electrically conductive wires 26 from the blood vessel 12, while leaving the band 44 encircled about the blood vessel 12. More particularly, a 0.013 inch transverse bore 50 is provided in the transducer head 14, specifically, through the encasing material 24. The securing means 46 comprises a longitudinally extending filamentous thread 48 slidably passing through the sheath 17 and slidably passing through the transverse bore 50. The thread 48 can conveniently be composed of nylon monofilament or another medical grade, biocompatible material.

As more clearly shown in FIGS. 2, 3, 5, 6, and 8, the thread 48 is preferably disposed in a pair of tubing segments 56 and 58 positioned in the sheath 17, entering the sheath 17 through a pair of 180 degree opposing holes 52 at the distal end 16 of the sheath 17, and exiting the sheath 17 through a proximal pair of holes 54 located between the distal end 16 and proximal end 42 of the sheath 17. The tubing segments 56 and 58 are conveniently composed of a medical grade, biocompatible material, preferably polyimide tubing. These segments are held in position in sheath 17 by silicone 80 that is injected into the bore of the sheath at its distal end. The proximal, remote holes 54 are preferably (although not necessarily) located outside the body of the patient when the band 44 holds the transducer head 14 on the blood vessel 12.

The thread 48 passes through the band 44, through the bore 50 and back through the band 44, to secure the transducer head 14, and, in particular, to secure the orientation fixing means 22 to the band 44. Severing of the thread 48 at any location along its length will allow it to be withdrawn from the vicinity of the band 44 and the bore 50, thereby detaching the transducer head 14 (more specifically, the orientation fixing means 22) from the band 44 and allowing the sheath 17, the transducer head 14 (including the transducer 18 and the orientation fixing means 22) and the wires 26 to be easily withdrawn from the patient without anaesthesia, discomfort, incision or other surgical intervention. Such severing of the thread 48 is most conveniently carried out by severing the thread 48 at a location 84 remote from the distal end 16 of the sheath 17.

The thread 48 can be configured as a simple closed loop. However, as more particularly shown in FIGS. 5 and 6, the thread 48 preferably includes first and second free ends 60 and 64 external to the sheath 17, exiting the sheath 17 through the holes 54. The first free end 60 of the thread 48 bears on it a graspable button 62, while the second free end 64 of the thread 48 exits the tubing segment 58 and is folded over it, then fixed to the outside of the tubing segment 58 by an overlying polyethylene shrink wrap tube 66. A plug or bead 68 composed of PTFE polymer (such as TEFLON) seals the open end 70 of the shrink wrap tube 66.

Figure 5:
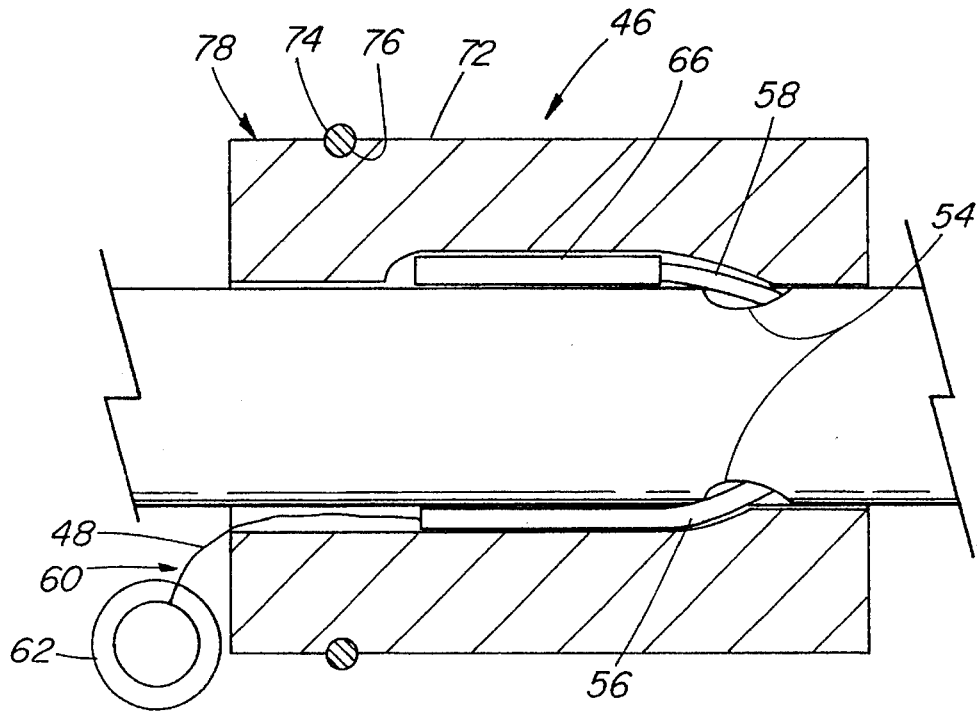
FIG. 5 is a partially sectioned and enlarged view of a mid portion of the preferred embodiment of the present invention of FIG. 1.

The free ends 60 and 64 of the thread 48, as well as their associated coverings, are frictionally retained against the sheath 17 by a removable silicone collar 72, which is also part of the securing means 46 (FIGS. 1 and 5). The collar 72 is longitudinally split and lies over the free ends 60 and 64 of the thread 48. The collar 72 is closed and held in position on the sheath 17 by a wrapping 74, e.g., a suture received in a circumferential groove 76 formed on the outer surface 78 of the collar 72. The collar 72 can be slid along the sheath 17 to ensure that a suitable tension is maintained on the thread 48 during introduction of the probe 10 and that the location 84 of severing of the thread 48 is readily available when removal of the probe 10 is desired.

Construction of the probe 10 according to the present invention is straightforward and should be readily understood from the foregoing details. However, encasement of the ultrasonic transducer 18 in the epoxy or other material 24 should be performed with due care. One convenient way to do this is to first attach the wires 26 to the transducer 18, then feed the wires 26 through the throughbores 33 in the ceramic tube 32. The desired angle of the operative surface 20 of the transducer 18 is established by manipulation, and a small drop of epoxy applied to the transducer 18 and ceramic tube 32 to prevent the angle from being altered during further assembly of the probe 10. Once the epoxy drop is cured, the ceramic tube 32 and the transducer 18 can be introduced into a silicone rubber mold, and epoxy injected into the mold to form the shape of the transducer head 14. Once the epoxy has cured, any flash or sharp contours can be ground off, and the transverse bore 50 drilled into the material 24.

Use of the probe 10 according to the present invention is straightforward as well. During or after a surgical procedure, and before wound closure, the band 44 is secured about the blood vessel 12 of interest by the sutures 82 in such a way as to abut the concave surface 30 of the encasing material 24 against the blood vessel 12. This affirmatively orients the operative surface 20 of the ultrasound transducer 18 with respect to the blood vessel 12. The plug 40 on the proximal, remote end 42 of the sheath 17 is connected to conventional ultrasound generating and sensing equipment, and the probe 10 is checked to ensure that it is properly monitoring the flow of blood within the vessel 12. The surgical incision is then closed, preferably (although not necessarily) leaving the collar 72 and the free ends 60 and 64 of the thread 48 outside the body of the patient. The velocity of blood in the blood vessel 12 is monitored for an appropriate time, for example, three to twenty-one days, to ensure the patency of the anastomosis and the patency of the transferred flap.

Once monitoring is no longer required, the probe 10 is easily removed from the patient by severing the thread 48 and releasing the transducer head 14, specifically, the orientation fixing means 22, from the band 44. More particularly, the collar 72 is surgically exposed and, if necessary, a razor employed to cut the wrapping 74. The collar 72 is then removed from the sheath 17, exposing the second free end 64 of the thread 48. The thread 48 is cut by scissors at the location 84, in particular, by cutting through the tubing segment 58 outside the sheath 17. The button 62 is then grasped and the first free end 60 of the thread 48 pulled to draw the thread 48 completely through the bore 50 and the band 44, and out one of the remote holes 54. Once the thread 48 is withdrawn, there is no other securement of the transducer head 14 or the orientation fixing means 22 to the band 44, and the sheath 17 and other elements of the probe 10 can be easily withdrawn from the body of the patient. The band 44, of course, remains in the patient, and may or may not become absorbed within the patient thereafter, depending upon its composition.

The present invention thus provides a pulsed Doppler ultrasound probe which is convenient to use, one which prevents detachment of the ultrasound transducer from the sheath carrying it, and which is easily removed after monitoring is complete, without entailing a surgical incision, excision or other technique, or anaesthesia or patient discomfort. The details of its construction or the composition of its various elements which are not otherwise disclosed are not believed to be critical to the achievement of its advantages, so long as the elements possess the strength or flexibility needed for them to perform as disclosed. The selection of these and other details of construction are believed to be well within the ability of one of even rudimentary skills in this area, in view of the present disclosure.

Industrial Applicability

The present invention is useful in the performance and monitoring of surgical procedures, and therefore finds applicability in human and veterinary medicine.

It is to be understood, however, that the above-described device is merely an illustrative embodiment of the principles of this invention, and that other devices and methods for using them may be devised by those skilled in the art, without departing from the spirit and scope of the invention. It is also to be understood that the invention is directed to embodiments both comprising and consisting of the disclosed parts.

What is claimed is:

1. A pulsed Doppler probe (10) for monitoring blood flow within a blood vessel (12), comprising:

a plurality of longitudinally extending electrically conductive wires (26) having distal ends (28);

an ultrasonic transducer (18) operatively connected to the distal ends (28) of the wires (26), the transducer (18) having an operative surface (20);

means (22) having a longitudinal axis (38) and fixing the orientation of the operative surface (20) of the ultrasonic transducer (18) with respect to at least one of the longitudinally extending electrically conductive wires and, the longitudinal axis (38)

a band (44) adapted to encircle the blood vessel (12); and remotely operable means (46) for detachably securing the orientation fixing means (22) to the band (44) so that the ultrasonic transducer (18) is positioned adjacent to the blood vessel (12);

whereby remote operation of the securing means (46) permits withdrawal of the ultrasonic transducer (18), wires (26) and orientation fixing means (22) from the blood vessel (12) while leaving the band (44) encircled about the blood vessel (12).

2. The probe (10) according to claim 1, wherein the orientation fixing means (22) comprises a material (24) encasing the ultrasonic transducer (18) and distal ends (28) of the wires (26).

3. The probe (10) according to claim 2, wherein the encasing material (24) is an epoxy.

4. The probe (10) according to claim 2, wherein the encasing material (24) is shaped to include a cylindrically concave surface (30).

5. The probe (10) according to claim 2, wherein the encasing material (24) includes a transverse bore (50), and the securing means (46) comprises a longitudinally extending thread (48) slidably passing through the transverse bore (50) in the encasing material (24).

6. The probe (10) according to claim 5, further comprising a sheath (17) containing the wires (26) and carrying the ultrasonic transducer (18) and the orientation fixing means (22).

7. The probe (10) according to claim 6, wherein the thread (48) passes through the sheath (17) and includes first and second free ends (60 and 64) external to the sheath (17).

8. The probe (10) according to claim 7, further comprising a removable collar (72) on the sheath (17), positioned over the first and second free ends (60 and 64) of the thread (48).

9. The probe (10) according to claim 8, wherein the collar (72) is longitudinally split, and the probe (10) further comprises a wrapping (74) about the collar (72) retaining the collar (72) on the sheath (17).

10. The probe (10) according to claim 9, wherein the collar (72) frictionally retains the first and second free ends (60 and 64) of the thread (48) against the sheath (17).

11. The probe (10) according to claim 1, wherein the securing means (46) comprises a longitudinally extending thread (48).

12. The probe (10) according to claim 1, wherein the band (44) is at least one of an absorbable material and an inert material.

13. The probe (10) according to claim 1, wherein the band (44) is configured as a mesh.

14. The probe (10) according to claim 1, further comprising a sheath (17) containing the wires (26) and carrying the ultrasonic transducer (18) and the orientation fixing means (22).

15. The probe (10) according to claim 14, further comprising a ceramic tube (32) connecting the sheath (17) and the orientation fixing means (22).

16. The probe (10) according to claim 15, wherein the ceramic tube (32) includes throughbores (33) in which the wires (26) are disposed.

17. The probe (10) according to claim 14, wherein the sheath (17) and the orientation fixing means (22) are generally circular in cross-section and have substantially the same diameter, thereby facilitating removal of the probe (10) upon operation of the securing means (46).

18. A pulsed Doppler probe (10) for monitoring blood flow within a blood vessel (12), comprising:

a longitudinally extending sheath (17) having a longitudinal axis (38);

a plurality of electrically conductive wires (26) extending longitudinally through the sheath (17), the wires (26) having distal ends (28);

an ultrasonic transducer (18) operatively connected to the distal ends (28) of the wires (26), the transducer (18) having an operative surface (20);

means (22) having a longitudinal axis (38) and fixing the orientation of the operative surface (20) of the ultrasonic transducer (18) with respect to at least one of the longitudinal extending wires and the longitudinal axis (38) of the orientation fixing means (22) and the sheath (17), the orientation fixing means (22) comprising an epoxy material (24) encasing the ultrasonic transducer

(18) and shaped to include a cylindrically concave surface (30);

a mesh band (44) of at least one of an absorbable material and an inert material, adapted to encircle the blood vessel (12); and remotely operable means (46) for detachably securing the orientation fixing means (22) to the mesh band (44) so that the ultrasonic transducer (18) is positioned adjacent to the blood vessel (12) and the concave surface (30) of the encasing material (24) faces the blood vessel (12);

wherein the securing means (46) comprises: (a) a transverse bore (50) through the encasing material (24); and (b) a longitudinally extending severable thread (48) slidably passing through the transverse bore (50) and the sheath (17), the thread (48) including first and second free ends (60 and 64) external to the sheath and remote from the encasing material (24); and wherein the sheath (17) and the orientation fixing means (22) are generally circular in cross-section and have substantially the same diameter, thereby facilitating removal of the probe (10) upon operation of the securing means (46).

19. The probe (10) according to claim 18, wherein the securing means (46) further comprises a removable collar (72) on the sheath (17), positioned over the first and second free ends (60 and 64) of the thread (48) so as to frictionally retain the first and second free ends (60 and 64) of the thread (48) against the sheath (17).

20. A pulsed Doppler probe (10) for monitoring blood flow within a blood vessel (12), comprising:

a longitudinally extending sheath (17) having a longitudinal axis (38);

a plurality of electrically conductive wires (26) extending longitudinally through the sheath (17), the wires (26) having distal ends (28);

an ultrasonic transducer (18) operatively connected to the distal ends (28) of the wires (26), the transducer (18) having an operative surface (20);

means (22) having a longitudinal axis 38 and fixing the orientation of the operative surface (20) of the ultrasonic transducer (18) with respect to at least one of the longitudinally extending wires (26) and the longitudinal axis (38) of the orientation fixing means (22) and the sheath (17), the orientation fixing means comprising an epoxy material (24) encasing the ultrasonic transducer (18) and shaped to include a cylindrically concave surface (30);

a ceramic tube (32) connecting the sheath (17) and the orientation fixing means (22), the wires (26) passing through the ceramic tube (32);

a mesh band (44) of at least one of an absorbable material and an inert material adapted to encircle the blood vessel (12); and remotely operable means (46) for detachably securing the orientation fixing means (22) to the mesh band (44) so that the ultrasonic transducer (18) is positioned adjacent to the blood vessel (12) and the concave surface (30) of the encasing material (24) faces the blood vessel (12);

wherein the securing means (46) comprises: (a) a transverse bore (50) through the encasing material (24); (b) a longitudinally extending severable thread (48) slidably passing through the transverse bore (50) and the sheath (17), the thread (48) including first and second free ends (60 and 64) external to the sheath and remote from the encasing material (24); and (c) a removable collar (72) on the sheath (17), positioned over the first and second free ends (60 and 64) of the thread (48) so as to frictionally retain the first and second free ends (60 and 64) of the thread (48) against the sheath (17); and wherein the sheath (17) and the orientation fixing means (22) are generally circular in cross-section and have substantially the same diameter, thereby facilitating removal of the probe (10) upon operation of the securing means (46).

* * * * *